(12) United States Patent
Tafti et al.

(10) Patent No.: US 9,289,280 B2
(45) Date of Patent: Mar. 22, 2016

(54) BIDIRECTIONAL VASCULAR FILTER AND METHOD OF USE

(71) Applicant: The Regents of the University of California, Oakland, CA (US)

(72) Inventors: Bashir A. Tafti, Los Angeles, CA (US); Edward W. Lee, Los Angeles, CA (US); Stephen T. Kee, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 6 days.

(21) Appl. No.: 14/585,795

(22) Filed: Dec. 30, 2014

(65) Prior Publication Data

US 2015/0366649 A1    Dec. 24, 2015

Related U.S. Application Data

(60) Provisional application No. 62/014,334, filed on Jun. 19, 2014.

(51) Int. Cl.
*A61F 2/01*    (2006.01)

(52) U.S. Cl.
CPC ............ *A61F 2/01* (2013.01); *A61F 2002/011* (2013.01); *A61F 2002/016* (2013.01); *A61F 2230/0076* (2013.01)

(58) Field of Classification Search
CPC ..... A61F 2/01; A61F 2/013; A61F 2002/016; A61F 2002/011; A61F 2230/0008; A61F 2230/0069; A61F 2230/0076
See application file for complete search history.

(56) References Cited

U.S. PATENT DOCUMENTS

| | | | |
|---|---|---|---|
| 5,350,398 A * | 9/1994 | Pavcnik et al. | 606/200 |
| 5,375,612 A * | 12/1994 | Cottenceau et al. | 128/899 |
| 6,059,814 A * | 5/2000 | Ladd | 606/200 |
| 6,267,776 B1 * | 7/2001 | O'Connell | A61F 2/01 606/158 |
| 6,428,558 B1 * | 8/2002 | Jones et al. | 606/200 |
| 6,511,496 B1 * | 1/2003 | Huter et al. | 606/200 |
| 6,558,405 B1 | 5/2003 | McInnes | |
| 6,610,077 B1 * | 8/2003 | Hancock et al. | 606/200 |
| 7,094,249 B1 * | 8/2006 | Broome et al. | 606/200 |
| 7,708,755 B2 * | 5/2010 | Davis et al. | 606/200 |
| 7,794,473 B2 | 9/2010 | Tessmer et al. | |
| 7,811,305 B2 * | 10/2010 | Balgobin | A61B 17/12022 606/191 |
| 8,308,752 B2 * | 11/2012 | Tekulve | 606/200 |
| 2001/0025187 A1 * | 9/2001 | Okada | 606/200 |
| 2005/0101987 A1 * | 5/2005 | Salahieh | 606/200 |
| 2005/0222604 A1 * | 10/2005 | Schaeffer | 606/200 |
| 2007/0005095 A1 | 1/2007 | Osborne et al. | |
| 2008/0275496 A1 * | 11/2008 | Fleming et al. | 606/200 |
| 2009/0062845 A1 * | 3/2009 | Tekulve | A61F 17/12022 606/213 |

(Continued)

OTHER PUBLICATIONS

International Search Report and Written Opinion, mailed Oct. 5, 2015; International Application No. PCT/US2015/036697, International Filing Date: Jun. 19, 2015. 9 Pages.

*Primary Examiner* — Ryan Severson
*Assistant Examiner* — Christian Knauss
(74) *Attorney, Agent, or Firm* — Riverside Law LLP

(57) ABSTRACT

The present invention relates to a device for filtering obstructive material within the vasculature of a subject. The device includes a generally ellipsoid shaped frame having a plurality of shape-memory arms with a collapsible, sieve-like structure positioned within the elliptical frame. The device may be used as an inferior vena cava (IVC) filter for the prevention of pulmonary embolism, or any other procedure requiring filtering of a vein.

30 Claims, 12 Drawing Sheets

(56) References Cited

U.S. PATENT DOCUMENTS

| | | | |
|---|---|---|---|
| 2009/0299402 A1* | 12/2009 | Orihashi et al. | 606/198 |
| 2009/0299403 A1 | 12/2009 | Chanduszko et al. | |
| 2009/0312748 A1* | 12/2009 | Johnson et al. | 606/1 |
| 2010/0152765 A1* | 6/2010 | Haley | A61F 2/01 |
| | | | 606/200 |
| 2012/0035646 A1* | 2/2012 | McCrystle | A61F 2/01 |
| | | | 606/202 |
| 2012/0041470 A1* | 2/2012 | Shrivastava et al. | 606/200 |
| 2013/0211495 A1* | 8/2013 | Halden et al. | 623/1.12 |
| 2014/0012310 A1* | 1/2014 | Urbanski et al. | 606/200 |
| 2014/0243878 A1* | 8/2014 | Urbanski | A61F 2/013 |
| | | | 606/200 |

* cited by examiner

BIDIRECTIONAL VASCULAR FILTER AND METHOD OF USE

CROSS-REFERENCE TO RELATED APPLICATIONS

This application claims priority to U.S. Provisional Application No. 62/014,334, filed on Jun. 19, 2014, incorporated herein by reference in its entirety.

BACKGROUND OF THE INVENTION

It is estimated that each year, between 300,000 and 600,000 people in the United States are negatively affected by deep vein thrombosis (DVT) and pulmonary embolism (PE). Further, it is estimated that between 60,000 and 100,000 people in the United States die each year as a result of venous thromboembolism (VTE), a disease that includes both DVT and PE, and occurs when a blood clot breaks loose and travels in the blood towards the lungs. Patients who are at risk of developing DVT or PE but cannot undergo anticoagulation therapy due to bleeding complications or ineffectiveness may opt for a vascular filter implant as an alternative treatment. Patients undergoing surgery for blunt trauma, penetrating trauma, and falls also benefit from vascular filters. These filters, commonly called inferior vena cava (IVC) filters, capture dislodged blood clots from the inferior vena cava and iliac veins before they can reach the lungs and heart.

A typical IVC filter consists of several wire legs arranged in a small conical shape. The filter is inserted into the IVC through either the jugular vein in the neck or the femoral vein in the groin, with the mouth of the cone facing towards the oncoming flow of blood. Barbs on the filter legs secure the filter to the internal walls of the vein, and the conical shape of the legs permits normal blood flow while capturing and holding loose blood clots and emboli.

After insertion, these filters may only be retrieved from one direction (the jugular or the femoral vein). Migration within the patient may cause the filter to tilt, positioning the retrieval hook in apposition to the blood vessel wall and out of reach of the filter retrieval device. The filter legs may also adhere to and even perforate the vessel wall, which may require an invasive surgical removal of the filter, increasing treatment costs and risk of complications to the patient. Further, a tilted filter changes the cross-sectional profile of the filter relative to the oncoming flow path of blood, which can lead to an inefficient and sub-optimal filter performance. Still further, some filters, such as the OPTEASE® IVC filter (Cordis Corp., Freemont, Calif., USA) have features at either pole that potentially push the incoming clot towards vessel walls and thereby increase the incidence of in-situ thrombus formation and filter occlusion. A recent attempt to create an improved retrievable IVC filter is the Crux® vena cava filter (Volcano Corp., San Diego, Calif., USA), which can be deployed and retrieved from either the jugular or femoral veins. However, the design of these types of filters leads to significant contact along the vessel wall and therefore does not minimize the problem of adhesions. Also, such elongated filters cannot be placed in patients with a short infrarenal IVC. Further, recent studies have also shown an increased incidence of DVT in patients with conventional filters, which may be linked to thrombotic occlusion of the filter leading to venous stasis upstream in the legs.

Thus, there is need in the art for a removable IVC filter that is less likely to adhere to a vessel wall, can be bidirectionally deployed and retrieved, minimizes the occurrence of tilt after deployment, minimizes the risk of vessel perforation, may be adjustable during deployment, and minimizes the occurrence of thrombotic occlusion in the filter. The present invention satisfies these needs.

SUMMARY OF THE INVENTION

The present invention relates to a device for filtering obstructive material within the vasculature of a subject. The device includes a generally ellipsoid shaped frame having a plurality of shape-memory arms with a collapsible, sieve-like web structure positioned within the ellipsoid frame. The device may be used as an IVC filter for preventing pulmonary embolism, or any other procedure requiring filtering of a vein.

Accordingly, the device relates to a vascular filter. The filter includes a frame having a plurality of ellipses each having a major axis and a minor axis, with the major axes of each ellipse overlapping one another in a proximal and distal direction, and a web positioned along its circumference to the minor axis of at least one ellipse, wherein the minor axes of the plurality of ellipses expand away from a central axis formed by their major axes, such that the web is held taut along its circumference when the plurality of ellipses are in an expanded state.

In one embodiment, the filter includes a hook coupled to the proximal end of the frame where the plurality of ellipses intersect at their proximal major axis vertices and a hook coupled to the distal end of the frame where the plurality of ellipses intersect at their distal major axis vertices. In another embodiment, the frame is composed of nonferromagnetic and flexible material. In another embodiment, the nonferromagnetic and flexible material is stainless steel. In another embodiment, the nonferromagnetic and flexible material is a shape-memory material. In another embodiment, the shape-memory material is Nitinol. In another embodiment, the web is positioned along its circumference to the minor axis vertices of each ellipse. In another embodiment, the web is fastened to at least one ellipse by a hook or loop. In another embodiment, the hook or loop is composed of a heat shrinking material. In another embodiment, the heat shrinking material is fluorinated ethylene propylene. In another embodiment, the web is composed of a plurality of crossing fibers. In another embodiment, the fibers are partially connected or bonded to each other. In another embodiment, the fibers are molded as a single unit. In another embodiment, the fibers are composed of a biocompatible material that is flexible, elastic, or both. In another embodiment, the fibers form a set of holes in the web. In another embodiment, the holes are sized between 3×3 mm and 10×10 mm. In another embodiment, the frame is compressible into a substantially cylindrical conformation, such that it fits within a catheter having a lumen of between about 3 F and 15 F. In another embodiment, the frame further includes at least one barb on the outer edge of the minor axis vertices of at least one ellipse. In another embodiment, the frame comprises 2 ellipses. In another embodiment, the frame comprises 3 ellipses.

In another embodiment, the vascular filter includes a frame having a plurality of hemi-ellipses each having a major axis and a semi-minor axis, with the major axes of each hemi-ellipse overlapping one another in a proximal and distal direction, and a web positioned along its circumference to the semi-minor axis of at least two hemi-ellipses, wherein the semi-minor axes of the plurality of hemi-ellipses expand away from a central axis formed by their major axes, such that the web is held taut along its circumference when the plurality of hemi-ellipses are in an expanded state. In another embodiment, the filter includes a hook coupled to the proximal end of the frame where the plurality of hemi-ellipses meet at their proximal major axis point and a hook coupled to the distal end of the frame where the plurality of hemi-ellipses meet at their distal major axis point. In another embodiment, the web is positioned along its circumference to the semi-minor axis vertex of the at least two hemi-ellipses. In another embodiment, the filter includes at least one barb on the outer edge of the semi-minor axis vertex of at least two hemi-ellipses. In another embodiment, the frame comprises 3 hemi-ellipses. In another embodiment, the frame comprises 5 hemi-ellipses. In another embodiment, the frame comprises 7 hemi-ellipses.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 11A is a perspective view, FIG. 11B is a top view and FIG. 11C is a side view of the deployment system engaged with the filter. FIGS. 11D and 11E are cross-sectional diagrams showing the securement tab engaged and the securement tab disengaged respectively.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical vascular filters. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

The present invention relates to a device for filtering obstructive material within the vasculature of a subject. As contemplated herein, the device may be used as an inferior vena cava (IVC) filter for the prevention of pulmonary embolism, or any other procedure requiring filtering of a vein.

Figure 1:
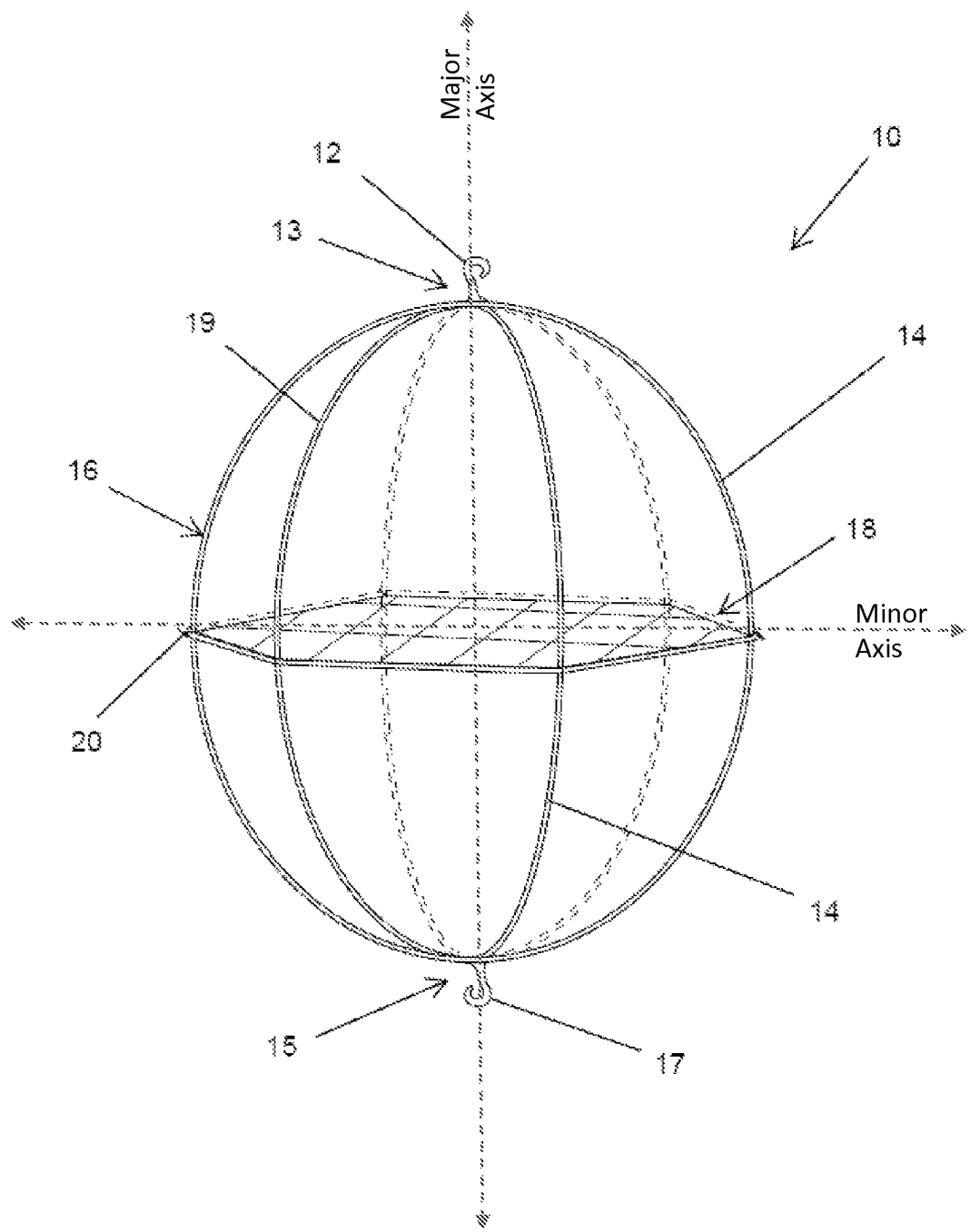
FIG. 1 is a perspective view of a filter according to an exemplary embodiment of the invention.

As shown in FIG. 1, the device 10 includes a frame 16 having a plurality of ellipses 14 connected at proximal base region 13 and distal base region 15. While there is no limitation to the number of ellipses 14, embodiments of the device 10 may include 2 ellipses, 3 ellipses, 4 ellipses, and even 5 or more ellipses. The ellipses 14 may be positioned equidistant from each other or they may be positioned variably such that the space between each is not uniform. Alternatively, the device 10 may be constructed as a frame 16 having a plurality of hemi-ellipses 19 connected at the proximal base region 13 and the distal base region 15. While there is no limitation to the number of hemi-ellipses 19 that could be used in the device 10, embodiments of device 10 may include 3 hemi-ellipses, 4 hemi-ellipses, 5 hemi-ellipses, 6 hemi-ellipses, and even 7 or more hemi-ellipses. Hemi-ellipses 19 may be positioned equidistant from each other or they may be positioned variably such that the space between each is not uniform. The filter 10 is bidirectional such that it is capable of equal filtering functionality of blood flow along the longitudinal axis in either the distal or proximal directions. Further, it is bidirectional in the sense that it can be advanced for delivery or retrieved for removal from either the proximal 13 or distal 15 sides of the device 10. The proximal 12 and distal 17 hooks are used to aid delivery and retrieval. They are preferably identical, however, it should be appreciated that there is no limitation to the size and/or shape of one or both of the hooks 12, 17.

In one embodiment, the frame 16 is composed of a nonferromagnetic, flexible, shape memory material, such as Nitinol. It should be appreciated that any rigid, yet flexible material may be used, such as a medical grade alloy or polymer, so that when the ellipses 14 or hemi-ellipses 19 are collapsed inwardly toward each other in a compressed state, an expanding bias is created, forcing ellipses 14 or hemi-ellipses 19 to return to their relaxed, expanded state. The medical grade materials described herein may also include an anti-thrombogenic coating or admixture to reduce the incidence of thrombus buildup, promoting hemocompatability and the maintenance of high blood flow rates through the filter.

In a preferred embodiment, a web element 18 is positioned within the ellipses 14 of the frame 16. As shown in the exemplary embodiment of FIG. 2, the web element 18 forms a type of sieve, web or mesh-like feature for capturing blood clot or emboli traveling through the blood stream. The web element 18 may be positioned approximately half way between the proximal base region 13 and the distal base region 15. In a preferred embodiment, the web element 18 is positioned on a plane perpendicular to the longitudinal axis extending between the proximal end 13 and the distal end 15 of the filter 10. It should be appreciated that the web 18 may be positioned at any distance along the longitudinal axis between the proximal end 13 and the distal end 15 of the filter 10, and further, may be positioned at any angle within the arms of frame 16 suitable for capturing blood clot and emboli.

Figure 2:
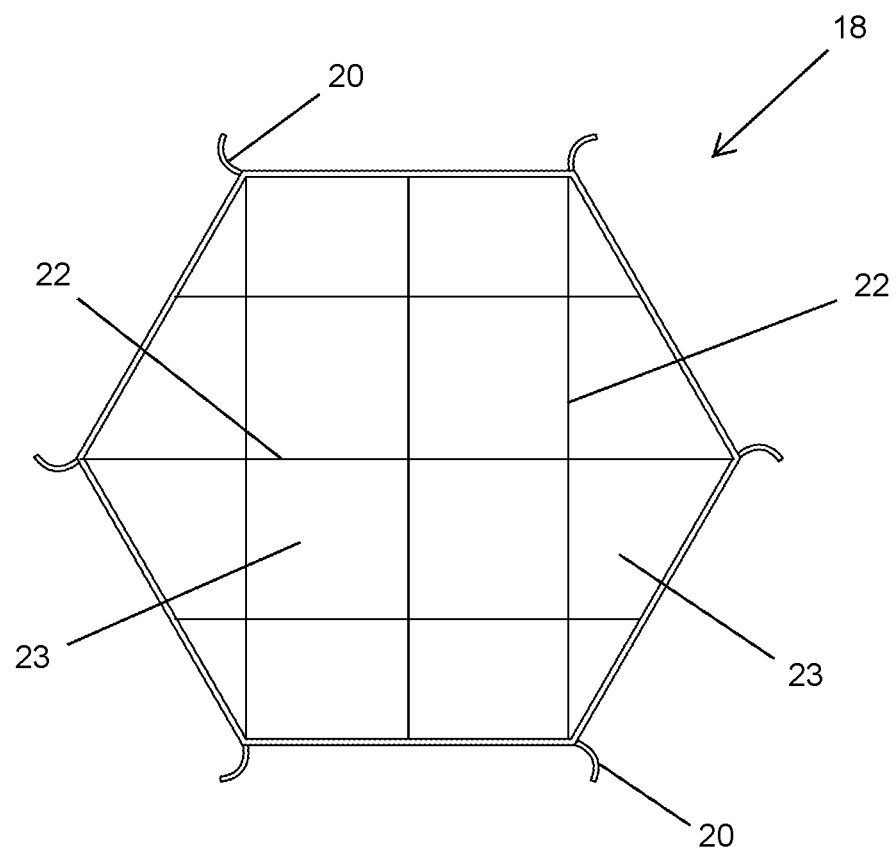
FIG. 2 is a top view of the web element shown in FIG. 1.
Figure 5:
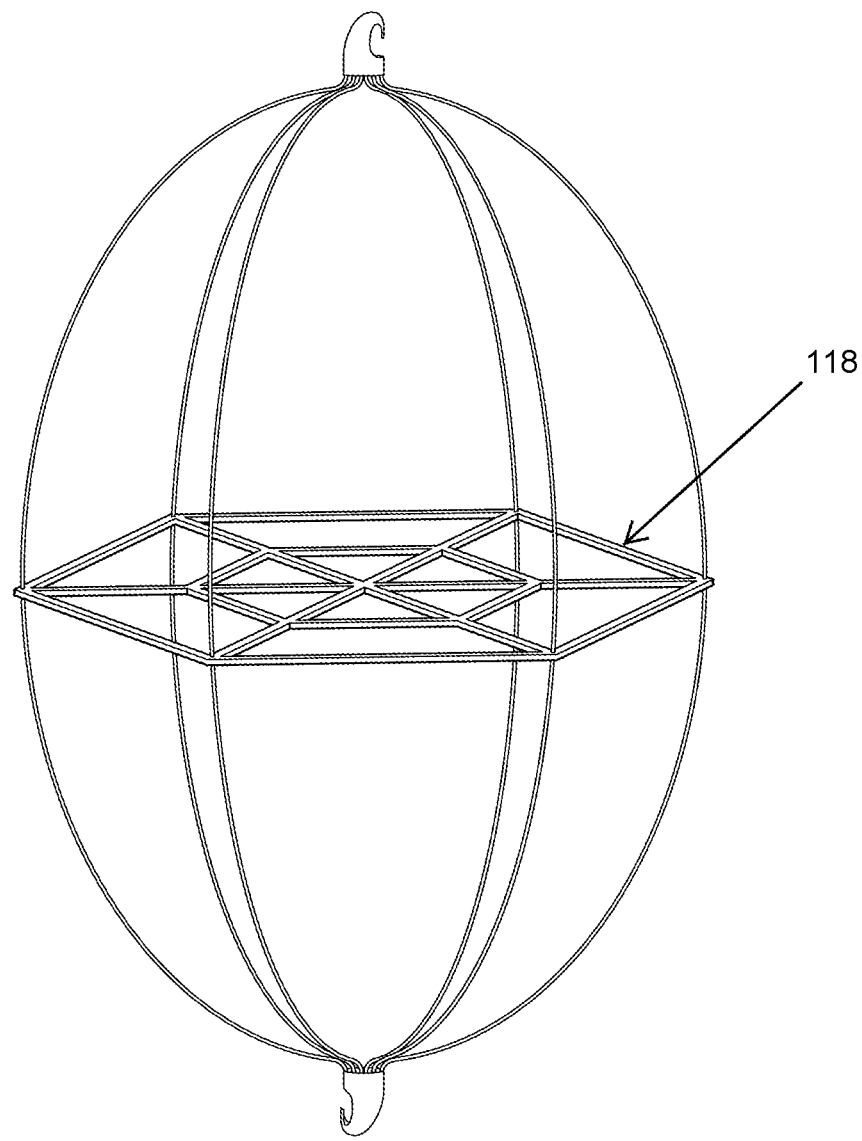
FIG. 5 is a side view of a filter with an alternative web pattern according to an exemplary embodiment of the invention.

As shown in FIG. 2, the web element 18 includes a plurality of crossing fibers 22 that form a mesh-like structure of openings 23. As contemplated herein, the fibers 22 of the web element 18 may be separate from each other, partially connected or bonded to each other, or alternatively they may be molded as a single unit. The fibers 22 of the web element 18 may form a randomly patterned set of variable sized openings, or it may be geometrically patterned to form openings of a specific and uniform size in either a symmetrical or asymmetrical pattern. The web element pattern could be a grid-like pattern as shown in the web element 18 of FIG. 2, or it could be more of a concentric triangular and trapezoidal pattern as shown in the alternative web element embodiment 118 of FIG. 5. For example, in one embodiment, with reference back to FIG. 2, the openings 23 are quadrilaterals of about 6×6 mm in size. In preferred embodiments, the openings 23 are preferably any size between 3×3 mm and 10×10 mm, and further may approximate any shape fitting within those dimensions. The web element 18 may further be a single layer of material or it may be a multi-layered material, such that the desired filtering rate and blood flow rate though the vein is achieved. The web element 18 can also include an anti-thrombogenic property as described above. The fibers 22 of the web element 18 can be composed of an alloy, polymer, or any other biocompatible material that is rigid and flexible, and/or elastic. Exemplary and non-limiting materials for constructing the web include Nitinol, ePTFE, PTFE, and the like.

Figure 3:
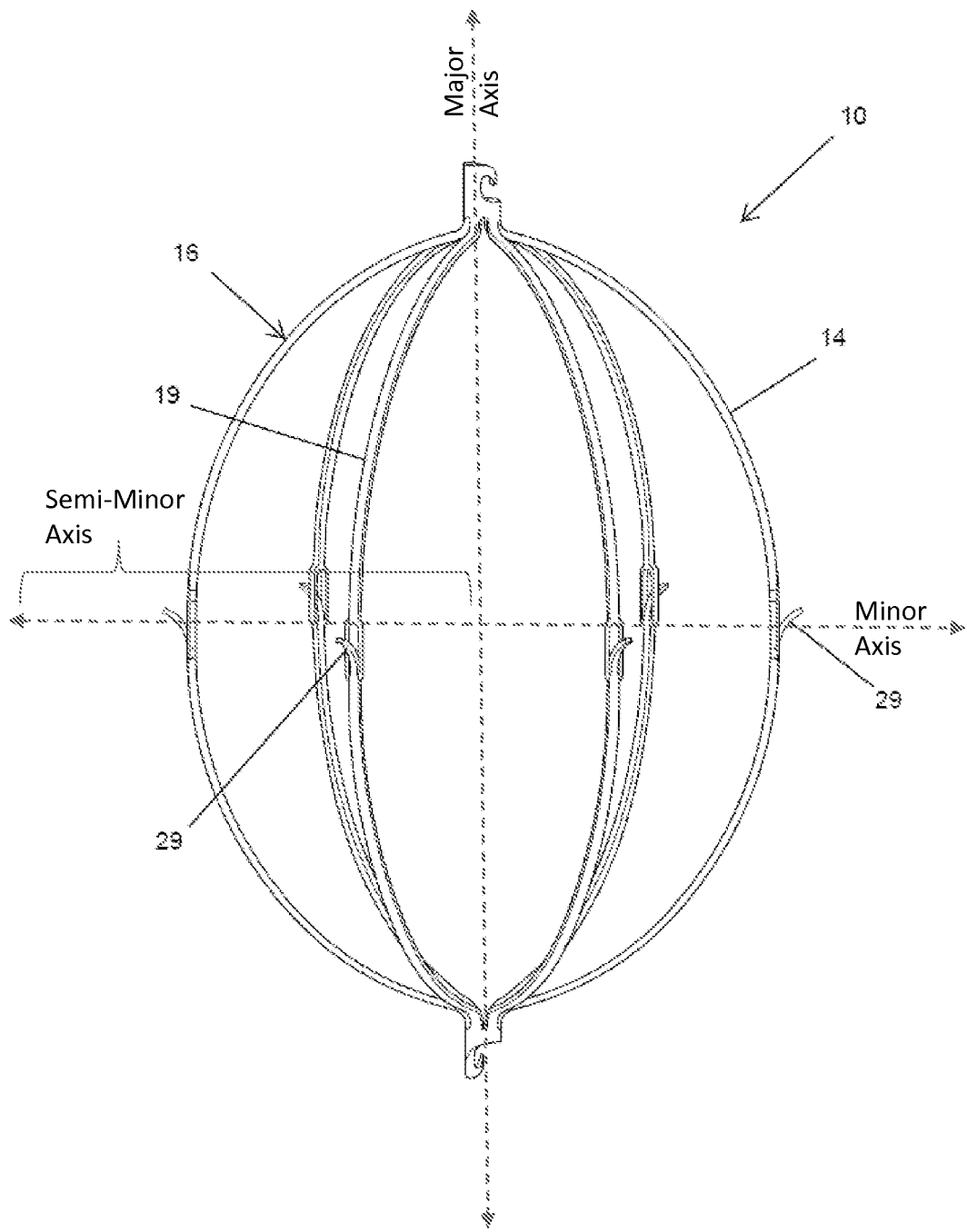
FIG. 3 is a side view of the filter shown in FIG. 1 with the web element removed and the detail of the barbs shown.
Figure 4C:
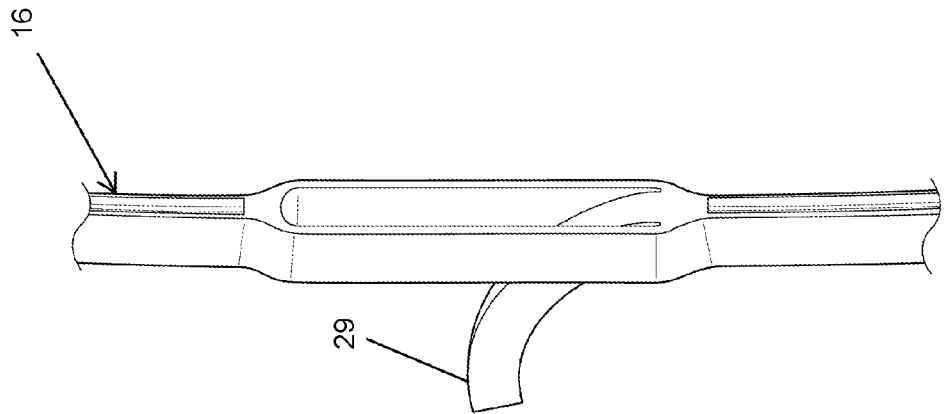
FIGS. 4A-4C show various magnified perspective side views of barbs according to the embodiment of the filter shown in FIGS. 1-3.
Figure 4B:
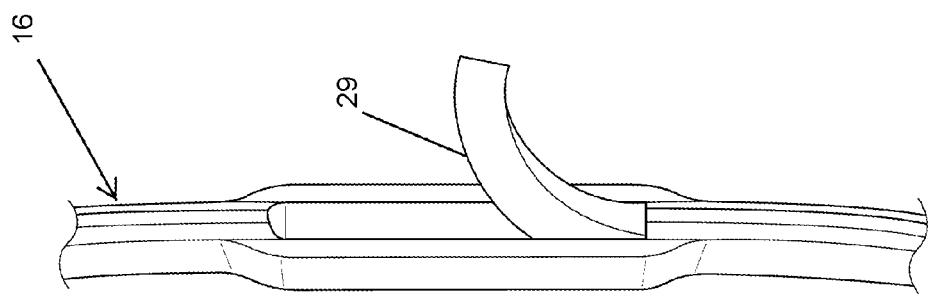
Figure 4A:
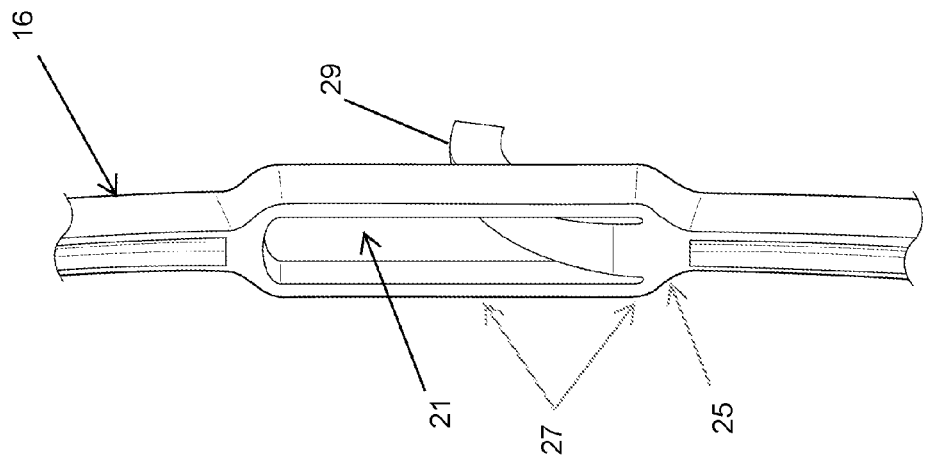

To prevent slippage of the filter 10 when positioned in a subject's vein and to anchor the device at a target treatment area, one or more barbs 29 may be positioned on a plane that bisects the filter's 10 longitudinal axis and runs along the minor axis of the ellipses 14 or the semi-minor axis of the hemi-ellipses 19 as shown in FIG. 3, or as shown with more detail in FIGS. 4A-4C. The barbs 29 secure and anchor the filter 10 against the patient's inner vessel wall as would be understood by those skilled in the art. Advantageously, since the barbs run along the path of the minor axis of the filter, a minimal footprint of contact with the inner vessel wall is achieved. The barbs can be on every ellipse along the minor axis as shown, or alternatively, can be present on alternate ellipses or any other combination of configurations. Barbs may project out from the filter perpendicularly, or otherwise be slanted in a proximal leaning or distal leaning direction. In alternate embodiments, barbs project out from the filter in a combination of perpendicular, proximally slanted, and distally slanted orientations. Barbs can also take a number of shapes, including curved, straight and variable thickness embodiments. With reference to the magnified views of FIGS. 4A-4C, the barbs are hinged at the bottom 25 of the openings 21, or at some portion 27 further up along the openings 21. The hinge acts as a strategic flex point so that while in a semi-collapsed or collapsed state, as the ellipses 14 collapse towards the center of the filter 10, the barbs 29 fold back about the flex point and into the openings 21, towards the middle of the device. In this state, the barbs remain tucked in below the outer surface of the filter 10. The hinge can be created structurally, for instance by the removal or reduction of framing 16 material (e.g. formation of the opening 21 itself), creating a weakened point of flexion along the frame 16 arm. Alternatively, the hinge can be created by a manufacturing step that incorporates a less rigid material at the desired flexion point, or by the introduction of additives that reduce material rigidity at the flexion point. Another method of forming the hinge includes a mechanical joint connecting two or more moving parts. Alternate embodiments do not have a hinge, and otherwise feature a contiguous member and composition of material along the length of the ellipse 14 and frame 16. Minimal exposure of the barbs above the surface of the filter 10 while in the semi-collapsed and collapsed states facilitates smooth advancement and retraction of the filter 10 during loading, placement and retrieval procedures. Further, the cross-sectional profile of the collapsed device is smaller and more spherical than conventional filters since the barbs tuck inward as opposed to being fixed and protruding out along outer surfaces of filter members. Advantageously, filters according to embodiments of the invention can fit into smaller delivery and retrieval catheters and devices, providing for minimized delivery and retrieval, and expanding treatment options for patients with a small or tortuous vein anatomy.

As shown in FIG. 1, the web element 18 can be coupled to the filter frame 16 at points along its circumference such that the web element lies along the minor axis of the filter 10. It should be appreciated that the web element 18 can be permanently secured to the frame 16, or it can be releasably secured to the frame 16 using methods known in the art or methods disclosed herein. For example, the web element 18 can include at least one hook or loop 20, as shown in FIG. 2, such that each hook or loop 20 is securely fastened to an arm of the frame 16. It should be appreciated that web element 18 can be coupled to only certain arms of the frame 16, and at any point along the length of the frame 16 arms, as desired. In another embodiment, the web element 18 is attached to the base of each barb 29 by fluorinated ethylene propylene (FEP) connections and secured by heat shrink processing.

In its relaxed state, the frame 16 expands the web element 18 so that each point of coupling between the web element 18 and the ellipses 14 or hemi-ellipses 19 holds the web element 18 substantially taut. When the frame 16 is compressed inwardly and towards the longitudinal axis of the filter 10, the web element 18 collapses within the frame 16 and assumes a much smaller profile, capable of sliding within the lumen of a delivery or retrieval device. The filter 10 can be sized so as to compress and collapse into a generally cylindrical conformation that fits within a standard catheter, sized to fit into a lumen of between about 3 F to 15 F. In one embodiment, the filter 10 is sized for use with a 6 F to 12 F catheter, and more preferably, a 6 F to 9 F catheter for delivery to or retrieval from the subject's vein.

Figure 6A:
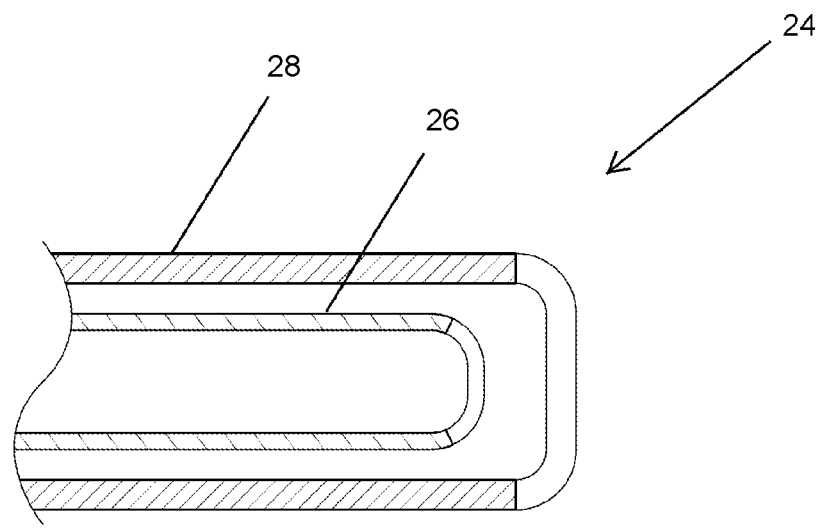
FIG. 6A is cross-sectional side view of a catheter delivery/retrieval system for filters according to various embodiments of the invention.

The filter 10 can be deployed into and retrieved from a subject's vein using a catheter-based system. As shown in the exemplary embodiment of FIG. 6A, the catheter system 24 includes an inner sheath 26 loaded within the lumen of an outer sheath 28. The filter 10 is compressed and collapsed into a thin cylindrical conformation such that it fits within the lumen of the inner sheath 26 as shown partially inserted in FIG. 6B. The filter 10 can be advanced forward by pushing the inner sheath 26 forward and pulled back by pulling on the snare 30. In a preferred embodiment and for ease of delivery, the filter 10 can be releasably coupled to a push rod 31 via the proximal hook 12 as shown in FIG. 7 (or alternatively the distal hook 17). In one embodiment, the push rod 31 may include a hook 32, loop, extension, or notch that engages with the proximal hook 12 as shown in FIG. 7. In this configuration, pushing on the push rod 31 may push the filter 10 out of the delivery sheath 26, expanding the filter 10 to its relaxed state and causing the perimeter of the filter 10 along the minor axis to engage the barbs 29 with the vessel wall, anchoring the filter at the point of treatment. Upon exiting the delivery sheath 26, the filter 10 can be decoupled from the push rod 31 by rotating push rod 31 along its longitudinal axis to disengage the notch 32 from the proximal hook 12. Alternatively, the push rod 31 need only contact an end of the filter 10, such that the filter 10 can be pushed out by the push rod 31 at the delivery site. In alternative embodiments, the filter 10 is deployable over a guidewire. Components at the proximal and distal ends of the filter 10, such as the proximal hook 12 and the distal hook 17, can include a guidewire lumen for loading the filter 10 over the guidewire. A retaining mechanism on the guidewire, such as a shaped section for forming an interference fit or other retaining mechanisms known in the art, can be used to secure the connection between the push rod 31 and the filter 10. During filter deployment within a vessel, once the filter 10 is advanced to a target position, the guidewire can be pulled back and retracted from its position within the filter 10, releasing the filter 10 from connection with the push rod 31, and allowing the push rod 31 to be withdrawn without dragging the filter from its target position. In certain embodiments, a vascular filter system includes a vascular filter device, having: a frame having multiple ellipses each having a major axis and a minor axis, with the major axes of each ellipse overlapping one another in a proximal and distal direction, a web positioned along its circumference to the minor axis of at least one ellipse, and a proximal hook coupled to the proximal end of the frame where the ellipses intersect at their proximal major axis vertices and a distal hook coupled to the distal end of the frame where the ellipses intersect at their distal major axis vertices; where the minor axes of the ellipses expand away from a central axis formed by their major axes, such that the web is held taut along its circumference when the ellipses are in an expanded state; and a guidewire; where the vascular filter device is configured to slidably load over the guidewire. The vascular filter device can have a guidewire lumen configured to coaxially load over the guidewire. The vascular filter system can also have an elongate deployment element and a retaining mechanism, wherein the retaining mechanism is configured to secure the elongate deployment element and the vascular filter device using the guidewire. The vascular filter system can also include an elongate deployment element and a retaining mechanism, where the retaining mechanism is configured to release the vascular filter device upon withdrawal of the guidewire from the vascular filter device.

Figure 6B:
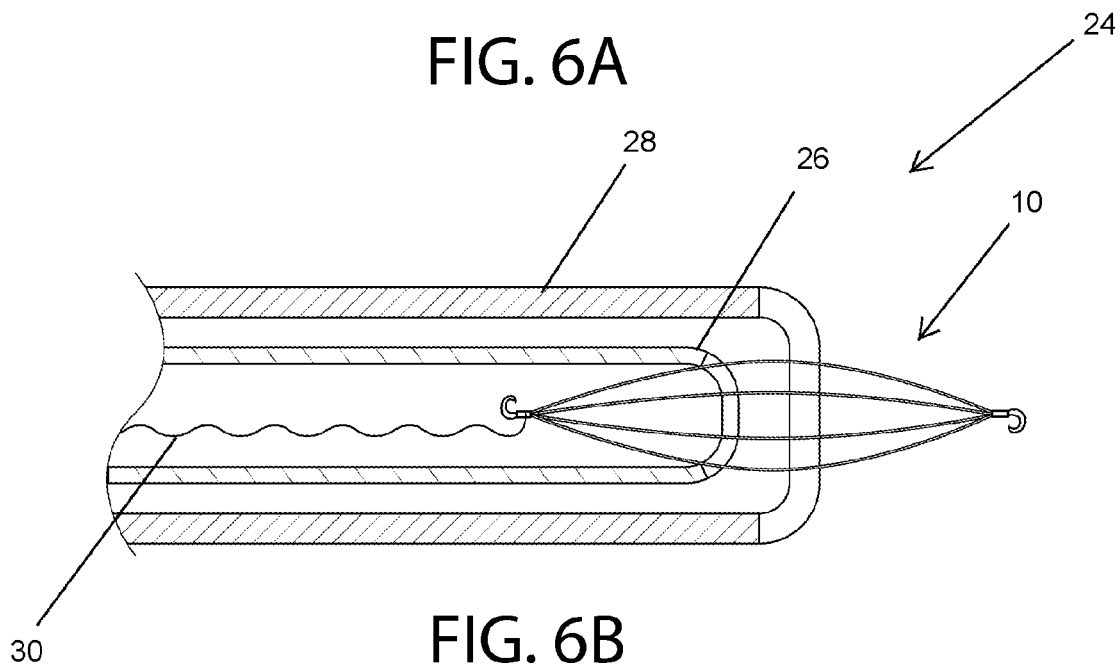
FIG. 6B is a cross-sectional side view of a catheter delivery/retrieval system with a filter in a semi-compressed state.
Figure 7:
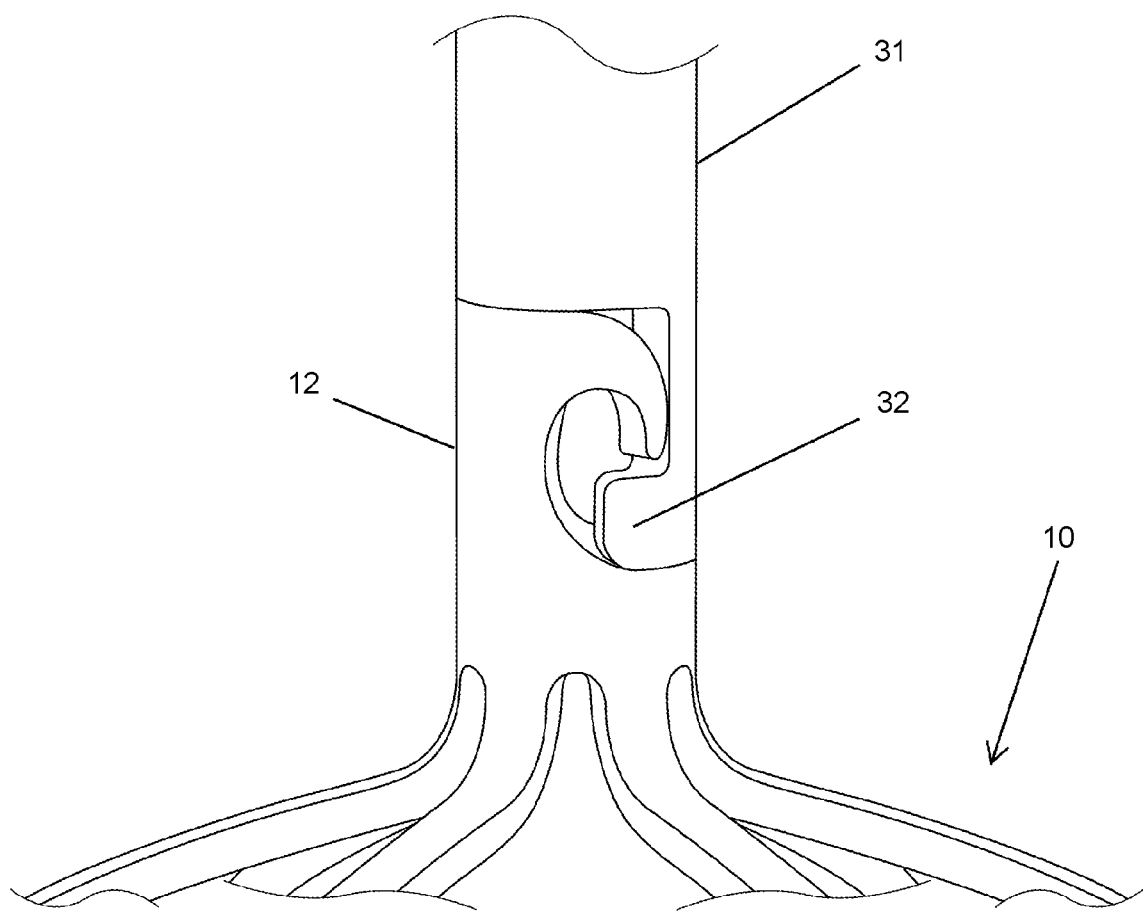
FIG. 7 is a magnified view of a push rod engaging a retrieval hook for deployment of the filter.

When retrieving the filter 10, a conventional snare 30 can latch onto the proximal hook 12 or the distal hook 17 of the filter 10, as shown in FIG. 6B. In this configuration, maintaining tension on the snare 30 will hold the filter 10 stationary while the inner sheath 26 is slipped over the filter 10 to compress and release the filter 10 from the blood vessel wall. The filter 10 can then be completely retracted within the lumen of the inner sheath 26, and the inner sheath 26 can be retracted back within the outer sheath 28 for removal from the patient.

Figure 8:
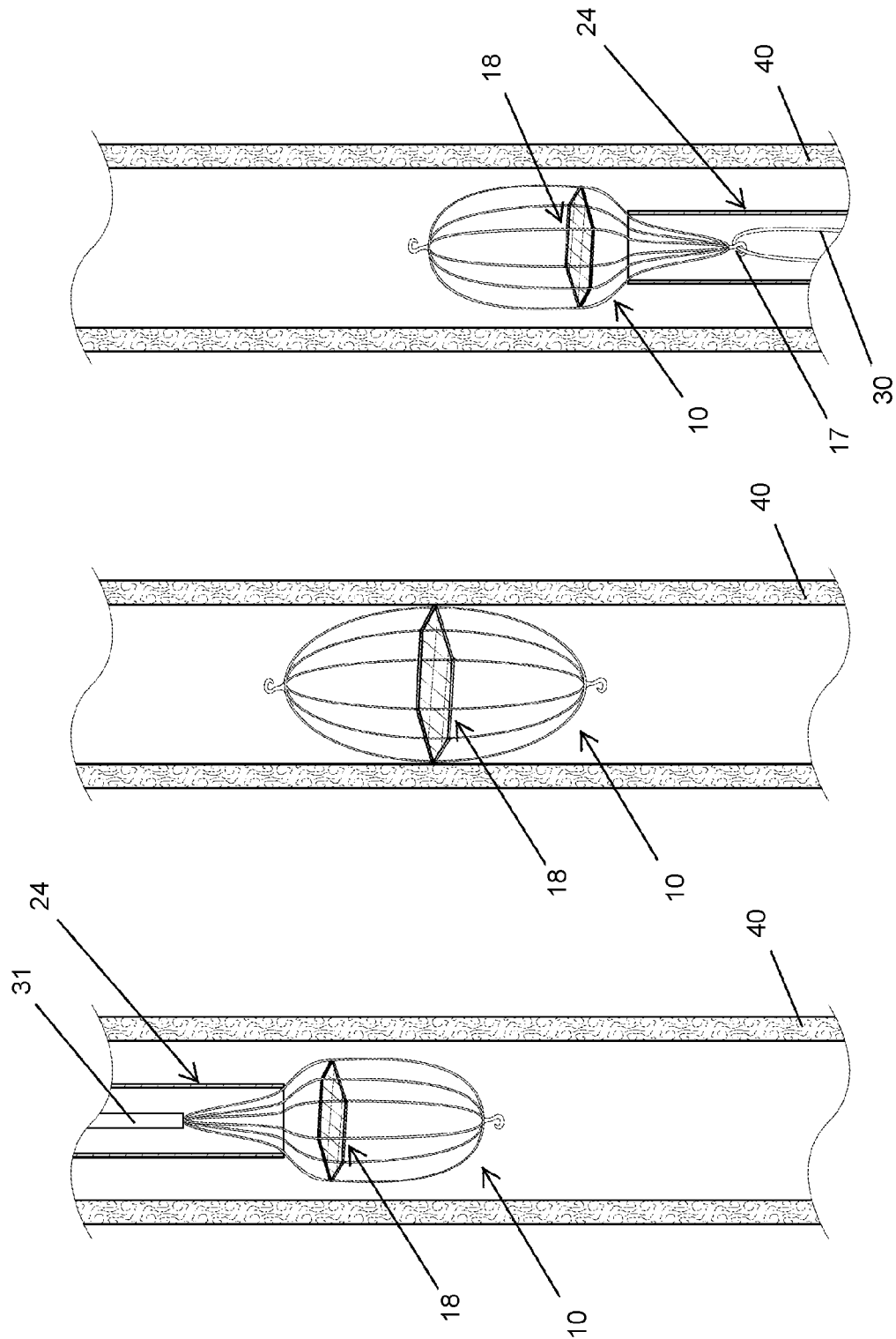
FIG. 8A is a side view of a filter partially deployed in a body vessel according to an exemplary embodiment of the invention.
FIG. 8B shows the filter fully deployed.
FIG. 8C shows the filter snagged by a retrieval member.
Figure 9:
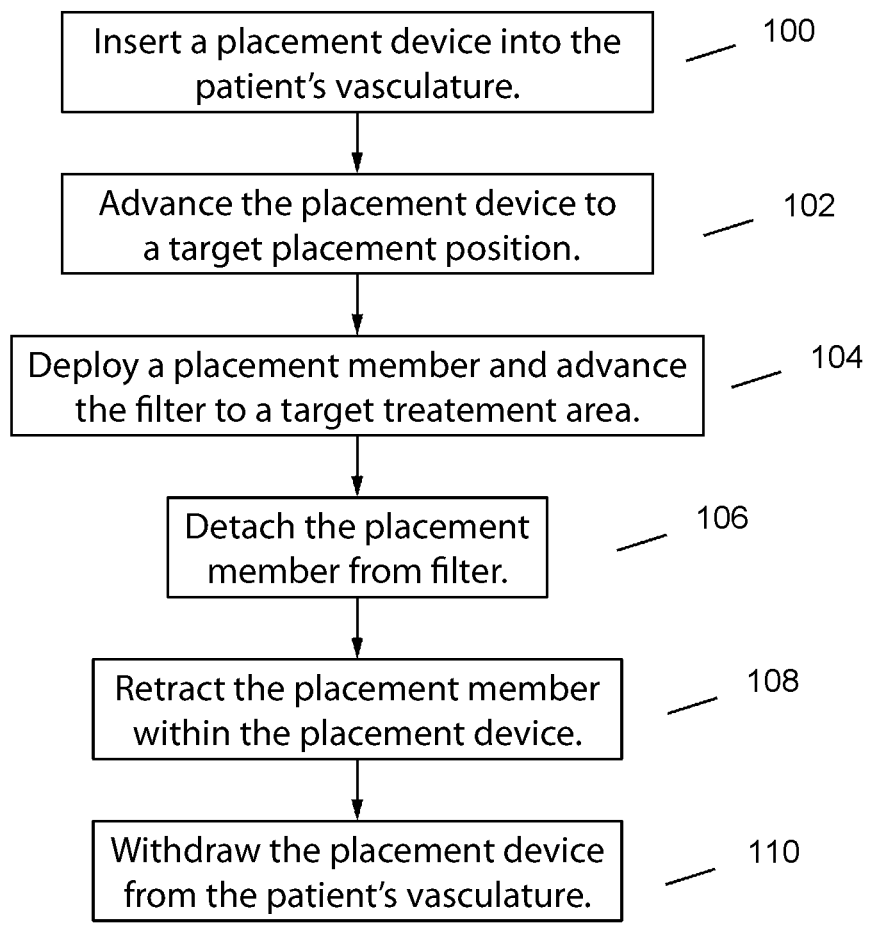
FIG. 9 is a flow chart of a method of filter placement.
Figure 10:
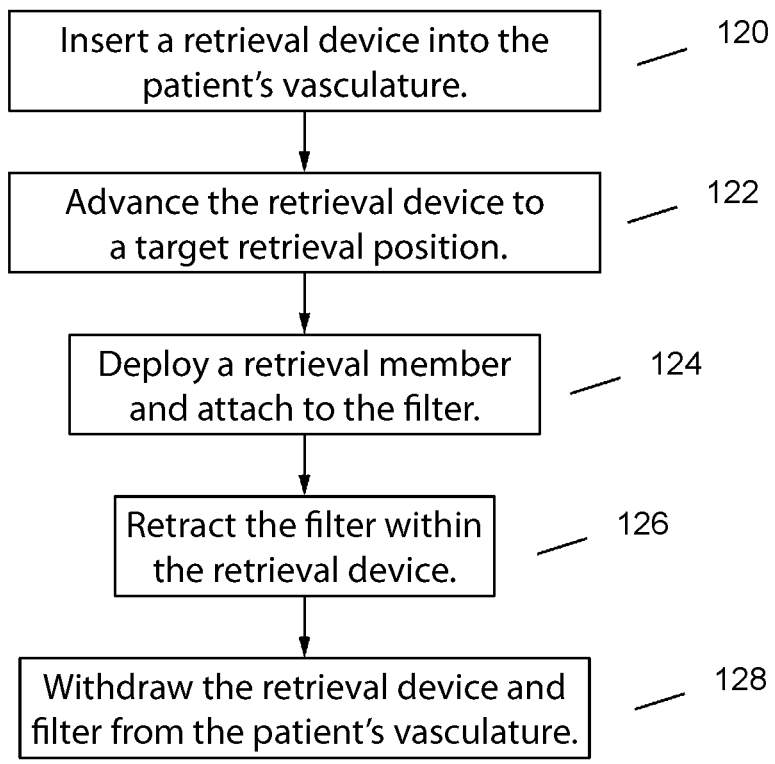
FIG. 10 is a flow chart of a method of filter retrieval.

The advantages and improved performance of the filter 10 disclosed herein is further illustrated in FIGS. 8A-8C, with reference to the flow charts in FIGS. 9 and 10 outlining an exemplary method of treatment. A method of treatment starts with the insertion and placement of the filter 10 into the patient's vasculature 40 via the placement device 100. Placement devices described herein or known in the art can be used to place the filter 10. As shown in FIG. 8A, the placement device is advanced to a target placement position 102 within the patient's vessel 40, and the placement member (such as a push rod 31) can be deployed for advancing the filter to a target treatment area 104 as shown in FIG. 8B. Once the filter 10 is properly positioned, the placement member can be detached from the filter 106, retracted back into the placement device 108, and the placement device can be withdrawn from the patient's vasculature 110. The web element 18 is anchored perpendicular to the longitudinal axis of the vessel by barbs positioned at the minor axis of the ellipse as described above. This design is advantageous to maintaining a consistent perpendicular profile of the web element in relation to the oncoming flow of blood, providing a more predictable and reliable filtering mechanism that is not prone to tilt. The counterbalance of the filter 10 also helps to minimize any chance of the web element 18 tilting post insertion. To remove the device, the retrieval device is inserted back into the patient's vascular 120. Retrieval devices known in the art or as described herein can be utilized. Since the filter 10 is bidirectional, it can be snagged from either jugular or femoral veins. As illustrated in FIG. 8C, the retrieval device is advanced to the target retrieval position 122 from a femoral vein. A snare 30 is deployed that grabs on to the distal hook 17, 122. Once attached, the filter is retracted into the retrieval device 126 and the retrieval device is withdrawn from the patient's vasculature 128. When the filter is to be deployed via the femoral route, in a preferred embodiment, a special delivery sheath or catheter needs to be used. Such a catheter consists of a resistant but flexible inner lining (e.g. a Nitinol lining) that can withstand penetration by the filter while being flexible enough to navigate through the vessels.

Figures 11A, 11B:
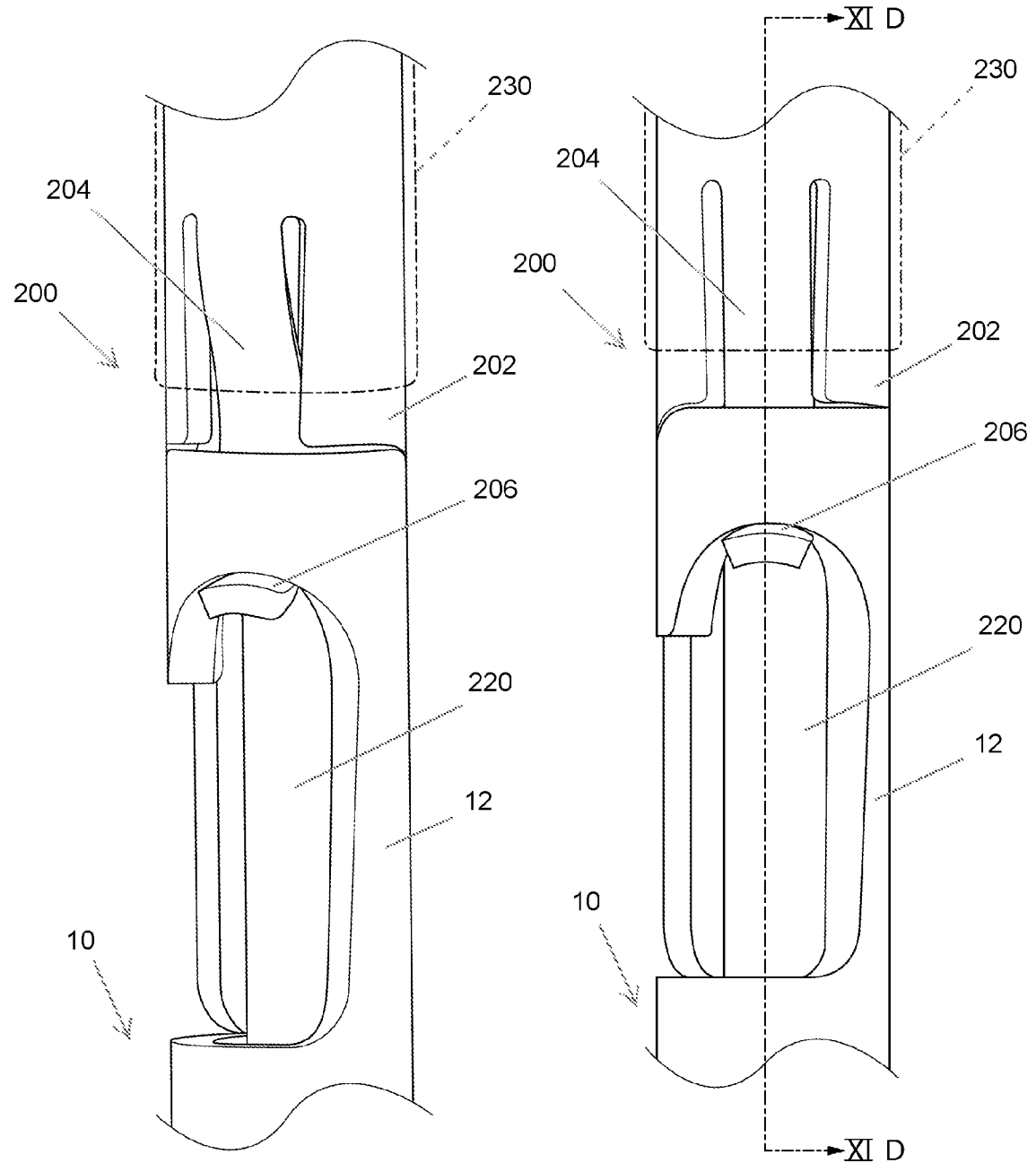
FIGS. 11A-11E show various views of a deployment system according to an alternate embodiment of the invention.
Figure 11C:
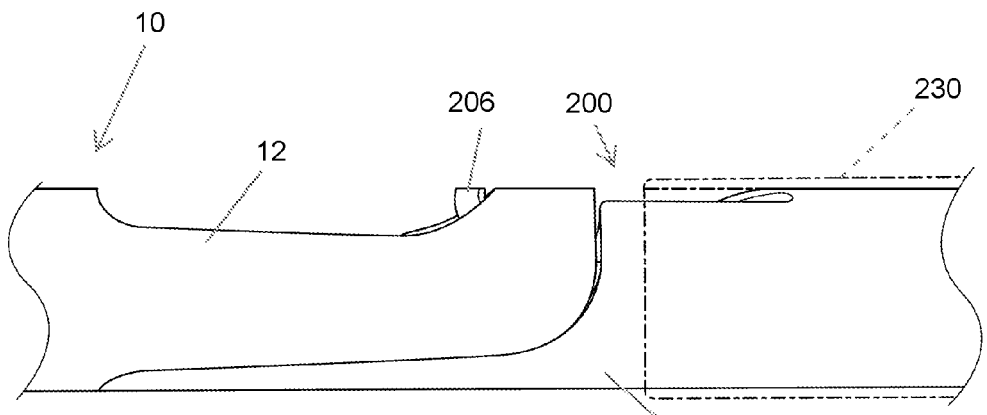
Figure 11D:
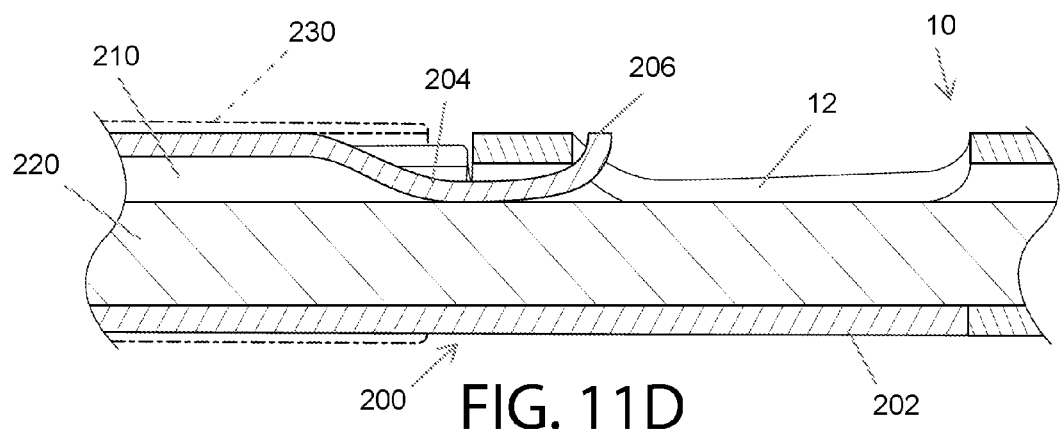
Figure 11E:
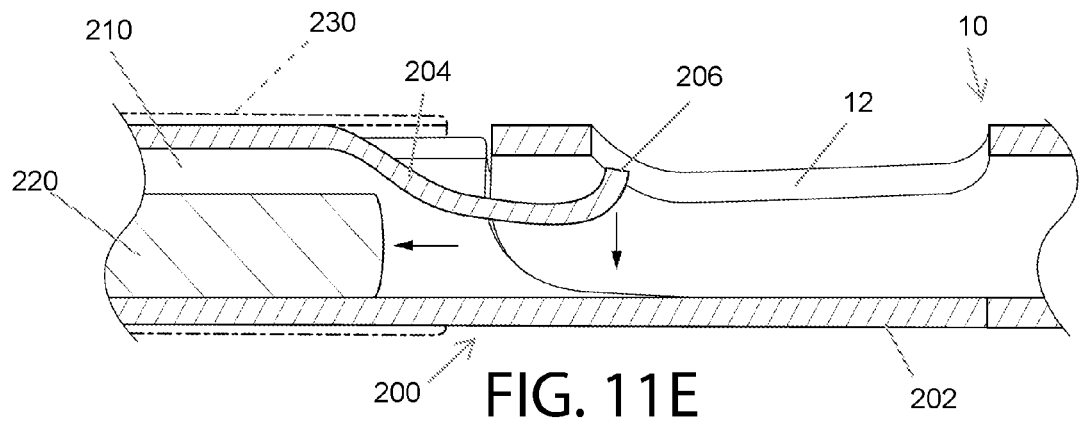

An alternative embodiment of a deployment system 200 is shown in FIGS. 11A-11E. The deployment system 200 has a deployment element 202 designed to engage with a filter hook 12 (or 17) for securing the filter during advancement into a vessel. The deployment element 202 is geometrically opposed to the outer surfaces of the filter hook 12 such that the connection maintains a tight circular profile. This circular profile allows a procedural sheath 230 to slide over the connection. A tab 204 built into the deployment element 202 has a securement protrusion 206 that can mate to the back of the hook 12 (or 17). As shown in FIGS. 11A, 11B, 11D and 11E, a wire 220, such as a conventional guidewire or stylet, is present in the lumen 210 during deployment of the system. The tab 204 is naturally biased in a recessed position, towards the center of the deployment system lumen 210 as illustrated in FIG. 11E. When the wire 220 is introduced within the lumen 210 and the tab is advanced under the hook 12, the wire 220 will keep the tab 204 pushed up, securing the tab 204 and the deployment element 202 to the hook as shown in FIG. 11D. When the wire 220 is removed from the lumen 210, the tab 204 recesses back into its relaxed state within the lumen 210 as shown in FIG. 11E, disengaging from the hook 12. At this point, the deployment element 202 can retracted away from the hook 12 and removed from the vessel. The deployment element 202 can be made of materials including medical grade plastics known in the art, and manufactured using an injection molding process. In alternative embodiments, the tab actuates by a control that remains external during deployment, such as a tether or a powered control as known in the art.

In some embodiments, the filter 10 can be used in conjunction with one or more drug-eluting materials, such as the Translute™ drug carrying polymer (Boston Scientific Co., Natick, Mass., USA) or other commercially available drug-eluting materials as would be understood by those skilled in the art. For example, the frame of the device may be coated with a polymer carrying an anticoagulant, anti-fibrosis, or cytotoxin. In this embodiment, the device may release medication in a targeted fashion, thereby enhancing the ability of the device to prevent DVT and PE. In other embodiments, the device can be manufactured from or coated with polymer admixtures (e.g. fluoropolymers) that promote device hemocompatability.

The device of the present invention marks a significant improvement over current IVC filters. First, the bidirectional design of the filter reduces error of the filter being inserted in the wrong direction. Further, the symmetrical design and the presence of hooks at both proximal and distal ends allows for the deployment and retrieval of the device from either end. Further still, the inclusion of a web creates a single unit device to better capture smaller materials in the bloodstream without the use of secondary, loose components. In addition, the hooks or barbs along the circumference of the frame secures the device with fewer and less traumatic points of contact with a blood vessel wall to facilitate easier and less traumatic removal. Also, the filter is less prone to tilt, which increases the performance of the filter, increases the flow rate of blood through the filter, minimizing the chance that the patient will develop complications such as venous stasis downstream of the filter or thrombotic occlusion of the filter, further providing health professionals with a more accurate and predictable filtering rate.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A vascular filter device, comprising:
a frame having a plurality of ellipses each having a major axis and a minor axis, with the major axes of each ellipse overlapping one another in a proximal and distal direction such that the plurality of ellipses share a single major axis; and
a web having a circumference that is positioned within the plurality of ellipses;
wherein the plurality of ellipses expand away from the shared major axis, such that the web is held taut along the circumference and is substantially perpendicular to the shared major axis when the plurality of ellipses are in an expanded state.

2. The device of claim 1, further comprising a proximal hook extending from a proximal end of the frame and a distal hook extending from a distal end of the frame.

3. The device of claim 1, wherein the frame is composed of a nonferromagnetic, flexible material.

4. The device of claim 3, wherein the nonferromagnetic, flexible material is a shape-memory material.

5. The device of claim 1, wherein the web circumference is positioned substantially at minor axis vertices of each ellipse.

6. The device of claim 1, wherein the web is fastened to at least one ellipse by a hook or loop.

7. The device of claim 6, wherein the hook or loop is secured by a heat shrinking material.

8. The device of claim 1, wherein the web is composed of a plurality of crossing fibers.

9. The device of claim 8, wherein the plurality of crossing fibers form a plurality of openings.

10. The device of claim 9, wherein the openings are sized between 3×3 mm and 10×10 mm.

11. The device of claim 1, wherein the frame is compressible about the shared major axis to achieve a substantially cylindrical conformation, such that the frame fits within a catheter having a lumen of between about 3 F and 15 F when the frame is compressed.

12. The device of claim 1, further comprising at least one barb on an outer edge of the minor axis of at least one ellipse.

13. A vascular filter device, comprising:
a frame having a plurality of hemi-ellipse shaped arms each having a proximal end and a distal end, wherein the proximal end of each hemi-ellipse shaped arm is connected to form a proximal frame end and the distal end of each hemi-ellipse shaped arm is connected to form a distal frame end, such that the frame has a central axis running through the proximal and distal frame ends; and
a web having a circumference that is positioned within the plurality of hemi-ellipse shaped arms;
wherein the hemi-ellipse shaped arms expand away from the central axis, such that the web is held taut along the circumference and is substantially perpendicular to the central axis when the plurality of hemi-ellipse shaped arms are in an expanded state.

14. The device of claim 13, further comprising a proximal hook extending from the proximal frame end and a distal hook extending from the distal frame end.

15. The device of claim 13, wherein the frame is composed of a nonferromagnetic, flexible material.

16. The device of claim 15, wherein the nonferromagnetic, flexible material is a shape-memory material.

17. The device of claim 13, wherein the web circumference is positioned substantially at semi-minor axis vertices of the at least two hemi-ellipse shaped arms.

18. The device of claim 13, wherein the web is fastened to at least two hemi-ellipse shaped arms by a hook or loop.

19. The device of claim 18, wherein the hook or loop is secured by a heat shrinking material.

20. The device of claim 19, wherein the heat shrinking material is fluorinated ethylene propylene.

21. The device of claim 13, wherein the web is composed of a plurality of crossing fibers.

22. The device of claim 21, wherein the fibers are composed of a biocompatible material that is flexible, elastic, or both.

23. The device of claim 21, wherein the fibers form a set of openings in the web.

24. The device of claim 23, wherein the openings are sized between 3×3 mm and 10×10 mm.

25. The device of claim 13, wherein the frame is compressible about the central axis to achieve a substantially cylindrical conformation, such that the frame fits within a catheter having a lumen of between about 3 F and 15 F when the frame is compressed.

26. The device of claim 13, further comprising at least one barb on an outer edge of the semi-minor axis of at least two hemi-ellipse shaped arms.

27. The device of claim 13, wherein the frame comprises at least 3 hemi-ellipse shaped arms.

28. A vascular filter system comprising:
a vascular filter device, comprising:
   a frame having a plurality of hemi-ellipse shaped arms each having a proximal end and a distal end, wherein the proximal end of each hemi-ellipse shaped arm is connected to form a proximal frame end and the distal end of each hemi-ellipse shaped arm is connected to form a distal frame end, such that the frame has a central axis running through the proximal and distal frame ends,
   a web having a circumference that is positioned within the plurality of hemi-ellipse shaped arms, and
   a proximal hook coupled to the proximal frame end and a distal hook coupled to the distal frame end;
   wherein the hemi-ellipse shaped arms expand away from the central axis, such that the web is held taut along the circumference and is substantially perpendicular to the central axis when the plurality of hemi-ellipse shaped arms are in an expanded state; and
a deployment system comprising:
   an elongate deployment element comprising a lumen and a tab biased toward a central axis of the lumen in a relaxed state, and
   a wire;
   wherein the deployment element is configured to accept advancement of the wire within the lumen, and
   wherein the tab is configured to secure at least one of the proximal and distal hooks to the deployment element in response to the wire being advanced under the tab.

29. A vascular filter system comprising:
a vascular filter device, comprising:
   a frame having a plurality of hemi-ellipse shaped arms each having a proximal end and a distal end, wherein the proximal end of each hemi-ellipse shaped arm is connected to form a proximal frame end and the distal end of each hemi-ellipse shaped arm is connected to form a distal frame end, such that the frame has a central axis running through the proximal and distal frame ends,
   a web having a circumference that is positioned within the plurality of hemi-ellipse shaped arms, and
   a proximal hook coupled to the proximal frame end and a distal hook coupled to the distal frame end;
   wherein the hemi-ellipse shaped arms expand away from the central axis, such that the web is held taut along the circumference and is substantially perpendicular to the central axis when the plurality of hemi-ellipse shaped arms are in an expanded state; and
a deployment system comprising:
   an elongate deployment element comprising a tab,
   wherein the tab is configured to secure at least one of the proximal and distal hooks to the deployment element.

30. The vascular filter system of claim 29, wherein the deployment system further comprises a tether for actuating the tab and releasing at least one of the proximal and distal hooks.

* * * * *